US00PP31843P2

(12) United States Plant Patent
Probst

(10) Patent No.: US PP31,843 P2
(45) Date of Patent: Jun. 2, 2020

(54) ***COREOPSIS* PLANT NAMED 'DARLING CLEMENTINE'**

(50) Latin Name: ***Coreopsis* hybrid**
Varietal Denomination: Darling Clementine

(71) Applicant: Darrell R. Probst, Hubbardston, MA (US)

(72) Inventor: Darrell R. Probst, Hubbardston, MA (US)

( * ) Notice: Subject to any disclaimer, the term of this patent is extended or adjusted under 35 U.S.C. 154(b) by 0 days.

(21) Appl. No.: 16/602,345

(22) Filed: Sep. 19, 2019

(51) Int. Cl.
*A01H 5/02* (2018.01)
*A01H 6/14* (2018.01)

(52) U.S. Cl.
USPC ..... Plt./417
CPC ..... *A01H 6/14* (2018.05)

(58) Field of Classification Search
USPC ..... Plt./417
CPC ..... A01H 5/02
See application file for complete search history.

*Primary Examiner* — Kent L Bell
(74) *Attorney, Agent, or Firm* — Penny J. Aguirre

(57) ABSTRACT

A new cultivar of hybrid *Coreopsis* plant named 'Darling Clementine' that is characterized by its compact plant habit reaching an average of 40 cm in height and 60 cm in width, its floriferous and long blooming season of its sterile inflorescences that do not require deadheading; bloom commences in mid-June and lasts until frost in Kensington, Conn., its large sized inflorescences with ray florets that are medium orange in color and flushed with yellow near the tips, its resistance to powdery mildew (*Podosphaera macularis*) and leafspot (*Pseudomonas cichorii*), and its cold hardiness at least to U.S.D.A. Zone 4.

2 Drawing Sheets

Botanical classification: *Coreopsis* hybrid.
Variety denomination: 'Darling Clementine'.

CROSS REFERENCE TO A RELATED APPLICATION

This application is related to a U.S. Plant Patent for a plant derived from the same breeding program that is entitled *Coreopsis* Plant Named 'Daybreak' (U.S. Plant Pat. No. 27,138).

BACKGROUND OF THE INVENTION

The present invention relates to a new and distinct cultivar of *Coreopsis* plant, botanically of hybrid origin and known as *Coreopsis* 'Darling Clementine' and will be referred to hereinafter by its cultivar name, 'Darling Clementine'. The new cultivar of *Coreopsis* is an herbaceous perennial grown for landscape and container use.

The new Invention arose from an ongoing controlled breeding program in New Braintree, Mass. The objective of the breeding program is to develop hybrid cultivars of *Coreopsis* with unique and superior garden attributes. In particular, to develop cultivars that are long-lived, sturdy, exhibit a true perennial habit and cold hardy to at least U.S.D.A. Zone 4 in a wide range of flower colors and plant forms.

The Inventor made a controlled cross in August of 2015 in New Braintree, Mass. between an unnamed and unpatented proprietary plant from his breeding program as the female parent (ref. code C 08-4) and pollen that was pooled from a variety of unnamed and unpatented proprietary plants from his breeding program as the male parent. The exact characteristics of the pollen parent are therefore unknown. 'Darling Clementine' was selected in September of 2016 as a single unique plant amongst the resulting seedlings.

Asexual propagation of the new cultivar was first accomplished by stem cuttings under the direction of the Inventor in Kensington, Conn. in September of 2016. Asexual propagation by stem cuttings has shown that the characteristics of the new cultivar are stable and are reproduced true to type in successive generations.

SUMMARY OF THE INVENTION

The following traits have been repeatedly observed and are determined to be the characteristics of the new cultivar. These attributes in combination distinguish 'Darling Clementine' as a unique cultivar of *Coreopsis*.

1. 'Darling Clementine' exhibits a compact plant habit reaching an average of 40 cm in height and 60 cm in width.
2. 'Darling Clementine' exhibits a floriferous and long blooming season of its sterile inflorescences that do not require deadheading; bloom commences in mid-June and lasts until frost in Kensington, Conn.
3. 'Darling Clementine' exhibits large sized inflorescences with ray florets that are medium orange in color and flushed with yellow near the tips.
4. 'Darling Clementine' exhibits resistance to powdery mildew (*Podosphaera macularis*) and leafspot (*Pseudomonas cichorii*).
5. 'Darling Clementine' exhibits cold hardiness at least to U.S.D.A. Zone 4.

The female parent of 'Darling Clementine' differs from 'Darling Clementine' in having flowers that are solid dark orange in color and in being very fertile causing flower production to stop once seed has set. 'Darling Clementine' can be most closely compared to *Coreopsis* cultivars 'Daybreak' (U.S. Plant Pat. No. 27,138) and 'Sunset Strip' (U.S. Plant Pat. No. 22,670). 'Daybreak' is similar to 'Darling Clementine' in being resistant to powdery mildew and leaf spot, in having a compact plant habit, in cold hardiness, and in having a long bloom season that does not require deadheading. 'Daybreak' differs from 'Darling Clementine' in having flower colors that are golden yellow with a maroon eye. 'Sunset Strip' is similar to 'Darling Clementine' in having inflorescences with ray floret colors that are orange with yellow tips. 'Sunset Strip' differs from 'Darling Clementine' in having finely dissected thread-leaf type foliage and in being very fertile therefore producing seed in abundance.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Publications include but are not limited to a listing on website by Romance Gardens, Skagit Horticulture, Phoenix Perennials, The National Gardening Association, Bachman's Wholesale, PlantAnt, James Greenhouses, and Emerald Cost Growers.

BRIEF DESCRIPTION OF THE DRAWINGS

The accompanying colored photographs illustrate the overall appearance and distinct characteristics of the new *Coreopsis*. The photographs were taken of a 4-month-old plant of 'Darling Clementine' as grown outdoors in a 1-gallon container in Kensington, Conn.

The photograph in FIG. 1 provides a side view of 'Darling Clementine' and shows the plant habit in bloom.

Figure 1:
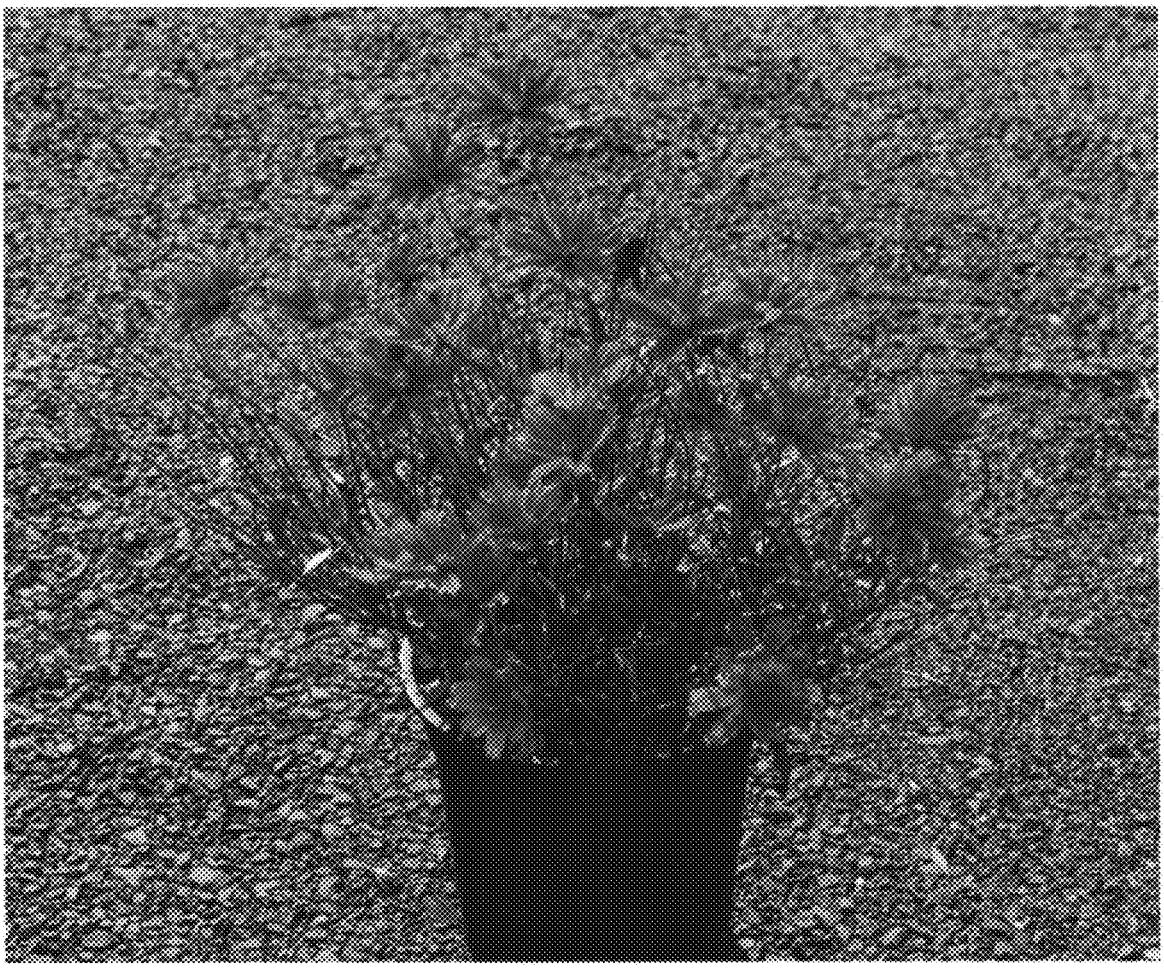
Figure 2:
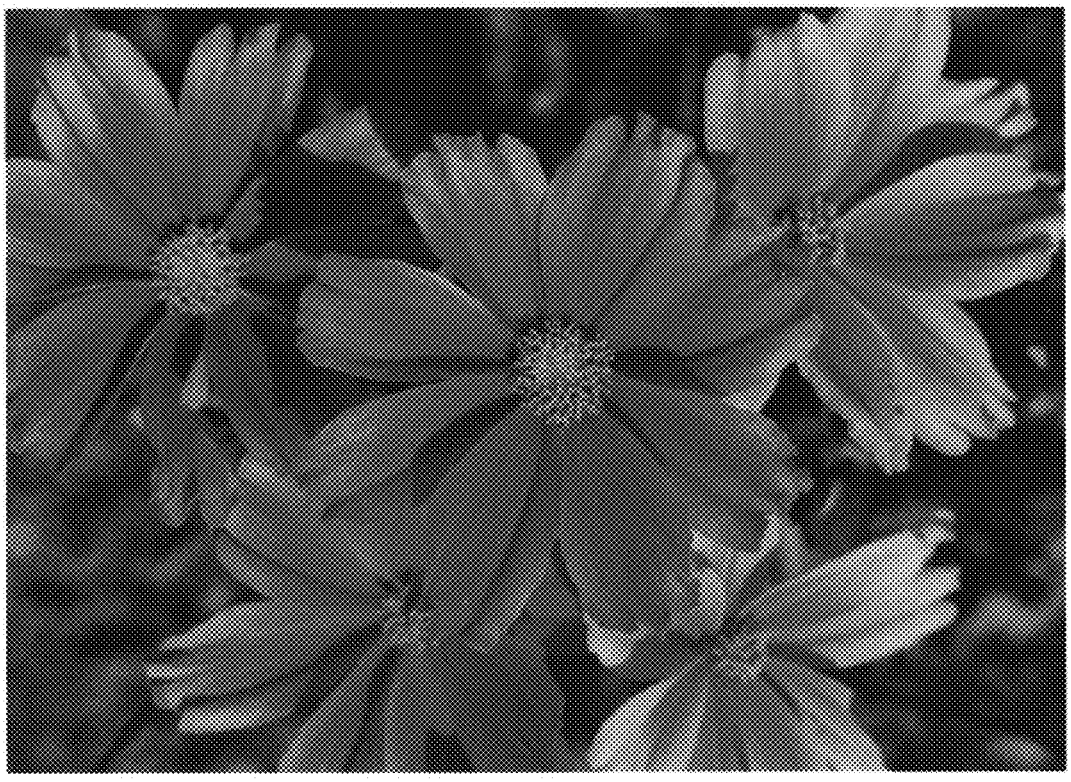

The photograph in FIG. 2 provides a close-up view of the inflorescences of 'Darling Clementine'.

The colors in the photographs are as close as possible with the photographic and printing technology utilized and the color values cited in the detailed botanical description accurately describe the colors of the new *Coreopsis*.

DETAILED BOTANICAL DESCRIPTION

The following is a detailed description of 4-month-old plants of 'Darling Clementine' as grown outdoors in one-gallon containers in Kensington, Conn. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—Blooms from mid-June until frost in Kensington, Conn.

*Plant type*.—Herbaceous perennial.

*Plant habit*.—Clump-forming, compact, upright leafy flowering stems with inflorescences held above the foliage.

*Height and spread*.—Reaching an average of 37 cm in height and 39 cm in width as grown in a one-gallon container and an average of 40 cm in height and 60 cm in width, as a mature plant in the landscape.

*Cold hardiness*.—At least to U.S.D.A Zone 4.

*Diseases and pests*.—Resistance to powdery mildew (*Podosphaera macularis*) and leafspot (*Pseudomonas cichorii*).

*Root description*.—Fibrous and fine, NN155A in color.

*Propagation*.—Stem cuttings.

*Time required for root initiation*.—An average of 10 days for root initiation.

*Growth rate*.—Vigorous, but stays compact.

Stem description:

*Shape*.—Rounded to tetragonal, solid.

*Stem color*.—144A.

*Stem strength*.—Strong.

*Stem size*.—Main stems; an average of 8 cm in length and 4 mm in width, lateral stems; an average of 11 cm in length (excluding peduncles) and 4 mm in width.

*Stem surface*.—Slightly glossy and moderately to densely covered with soft pubescence, up to 1 mm in length and NN155A in color.

*Branching habit*.—Freely branched, an average of 8 basal main stems, lateral stems typically branched as oppositely arranged pairs at each node, with an average of 4 lateral stems (2 pairs) per main stem.

*Internode length*.—An average of 4 cm.

Foliage description:

*Leaf division*.—Simple.

*Leaf margins*.—Entire, bi-fid and trifid.

*Leaf size*.—Entire leaves; an average of 7 cm in length and 4 cm in width, trifid leaves; center lobe an average of 5 cm in length and 6 mm in width, lateral lobes an average of 2 cm in length and in 2 mm width.

*Leaf shape*.—Narrow obanceolate.

*Leaf base*.—Cuneate.

*Leaf apex*.—Bluntly acute.

*Leaf venation*.—Pinnate, inconspicuous, same color as leaf.

*Leaf attachment*.—Sessile.

*Leaf arrangement*.—Opposite.

*Leaf surface*.—Upper and lower surfaces; dull and sparsely to moderately covered with stiff pubescence, especially along the margins; up to 1 mm in length, NN155A in color.

*Leaf color*.—Young and mature upper and lower surface; 144A.

Flower description:

*Inflorescence type*.—Composite with a single row of ray florets surrounding disk florets in the center, forming a radiant head, inflorescences are borne on branch terminals in loose corymbs.

*Lastingness of inflorescence*.—8 to 10 days until senescence of ray florets, phyllarys and disk florets are persistent.

*Fragrance*.—Very faint pleasant scent.

*Quantity of inflorescences*.—Free flowering, an average of 4 corymbs per main branch, an average of 3 composites per corymb.

*Inflorescence size*.—Corymbs; an average of 19 cm in length and 8 cm in width, composite; an average of 3 cm in depth and 5 cm in diameter with disk portion up to 6 mm in diameter.

*Inflorescence buds*.—Globose in shape, an average of 6 mm in depth and diameter, smooth and shiny surface; color; a blend of 143A and N144A.

*Peduncle*.—Rounded in shape, strong, an average of 15 cm in length and 1 mm in diameter, 144A in color, smooth and glabrous surface.

Phyllaries (involucral bracts):

*Phyllary number*.—2 rows; outer (lower) row 8, inner (upper) row 8.

*Phyllary arrangement*.—Outer (lower) phyllaries; 5% fused, held horizontal to slightly upwards with the apex and mid-section recurved downwards, inner (upper) phyllaries; overlap and surround receptacle with apical portion reflexed (campanulate-like).

*Phyllary size*.—Outer (lower) phyllaries; an average of 5 mm in length and 3 mm in width, inner (upper) phyllaries; an average of 1 cm in length and 5 mm in width.

*Phyllary color*.—Upper and lower surfaces, outer (lower) phyllaries; 143A, margins 142B, inner (upper) phyllaries; translucent, 151A.

*Phyllary texture*.—Outer (lower) phyllaries; glabrous and smooth on both surfaces, inner (upper) phyllaries; glabrous and slightly waxy on both surfaces.

*Phyllary apex*.—Acute.

*Phyllary base*.—Truncate.

*Phyllary shape*.—Outer (lower) phyllaries; elliptic to lanceolate, inner (upper) phyllaries; lanceolate.

Ray florets (sterile):

*Number*.—8.

*Shape*.—Oblanceolate, with the appearance of 3 to 4 longitudinal sections.

*Size*.—An average of 2.1 cm in length and 1.5 cm in width.

*Apex*.—Rounded with rounded lobes.

*Base*.—Cuneate.

*Margins*.—Entire on sides with lobed and notched apex.

*Aspect*.—Held mainly horizontal and slightly upwards, perpendicular to peduncle.

*Texture*.—Both surfaces; glabrous, dull, and satiny.

*Color*.—Upper surface when opening and fully open; 14A, flushed at the base to mid- section with N34A, lower surfaces when opening and when fully open; 14A, base lightly flushed with 14A, the area flushed with N34A increases as the florets mature.

Disk florets (male and female):

*Number*.—An average of 100.

*Shape*.—Tubular, corolla is fused, flared and slightly curled at apex.

*Size*.—About 5 mm in length and 0.4 mm in width.

*Color*.—En masse; a blend of 14A and 24A, corolla; (tube) base and mid-section translucent, 145A, top below flare 145A, flared portion 24A to 14A.

*Receptacle*.—An average of 6 mm in diameter and 3 mm in depth, 144A in color.

Reproductive organs:

*Presence*.—Disk florets only.

*Gynoecium*.—1 Pistil; an average of 5 mm in length, style; very fine and 23A in color, bifid pillose, stigma; 24A to 14A in color with recurved branches about 1 mm in length, ovary is inferior, oblong in shape, an average of 2 mm in length and 1 mm in width, and 145A in color.

*Androecium*.—4 stamens, fused into tube surrounding style, an average of 3 mm in length and less than 0.5 mm in width, 200B in color, no pollen was present.

*Seed*.—Seed development has not been observed.

It is claimed:

1. A new and distinct cultivar of *Coreopsis* plant named 'Darling Clementine' as herein illustrated and described.

* * * * *